United States Patent [19]
Vallee et al.

[11] Patent Number: 5,852,001
[45] Date of Patent: Dec. 22, 1998

[54] METHOD AND COMPOUNDS FOR INHIBITION OF RIBONUCLEASES

[75] Inventors: Bert L. Vallee; Aniello Russo, both of Brookline, Mass.

[73] Assignee: The Endowment for Research in Human Biology, Boston, Mass.

[21] Appl. No.: 772,620

[22] Filed: Dec. 23, 1996

[51] Int. Cl.$^6$ .................. A61K 31/70; C07H 19/207
[52] U.S. Cl. .................. 514/47; 514/48; 514/51; 536/26.22
[58] Field of Search .................. 536/26.22; 514/47, 514/51, 48

[56] References Cited

U.S. PATENT DOCUMENTS

| | | | |
|---|---|---|---|
| 3,321,463 | 5/1967 | Moffatt | 536/26.22 |
| 3,709,873 | 1/1973 | Fujimoto | 536/26.22 |
| 4,721,672 | 1/1988 | Vallee et al. | 435/70 |
| 4,897,464 | 1/1990 | Vallee et al. | 530/350 |
| 4,900,673 | 2/1990 | Harper et al. | 435/199 |
| 4,916,073 | 4/1990 | Vallee et al. | 435/252.3 |
| 4,966,849 | 10/1990 | Vallee et al. | 435/199 |
| 4,966,964 | 10/1990 | Shapiro et al. | 536/23.51 |
| 5,266,687 | 11/1993 | Shapiro et al. | 536/23.1 |
| 5,270,204 | 12/1993 | Vallee et al. | 435/252.3 |
| 5,286,487 | 2/1994 | Vallee et al. | 424/94.6 |
| 5,520,914 | 5/1996 | Fett et al. | 424/158.1 |

FOREIGN PATENT DOCUMENTS

| 0291686 | 11/1988 | European Pat. Off. . |
| 9112322 | 8/1991 | WIPO . |

OTHER PUBLICATIONS

Sambrook, Fritsch & Maniatis, 1989, *Molecular Cloning: A Laboratory Manual*; pp. 7.3–7.5 Cold Spring Harbor Laboratory Press, Cold Spring Harbor, NY. Month of publication data is unavailable.
Beintema, J.J., 1987, *Life Chemistry Reports* 4:333–389. Month of publication data is unavailable.
Richards, F.M. and Wyckoff, H.W., 1971 *Enzymes Bovine Pancreatic Ribonuclease* 4:647–806. Month of publication data is unavailable.
Nogues, M.V., Vilanova, M. & Cuchillo, C.M., 1995, *Biochimica et Biophysica Acta* 1253:16–24. Month of publication data is unavailable.
Eftink, M.R., & Biltonen, R.L., 1987 *Hydrolytic Enzymes*, 333–376. Month of publication data is unavailable.
Lee, F.S. and Vallee, B.L., 1993, *Progress in Nucleic Acid Research and Molecular Biology* 44:1–30. Month of publicatoin data is unavailable.
Lindquist, R.N., Lynn Jr., J.L., & Lienhard, G.E. Dec. 26 1973 *Journal of the American Chemical Society* 95:8762–8768.
Wlodawer, A., Miller, M., & Sjolin, L., 1983, *Proc. Natl. Acad. USA* 80:3628–3631 (Jun. 1983).
Berger, S.L. & Birkenmeier, C.S. 1979 *Biochemistry* 18:5143–5149 (Issue No. 23). Month of publication data is unavailable.
Iwahashi, K., Nakamura, K.T., Mitsui, Y., Ohgi, K. & Irie, M. 1981, *J. Biochem.* 90:1685–1690 (Issue #6). Month of publication data is unavailable.
White, M.D., Bauer, S. & Lapidot, Y. 1977, *Nucleic Acid Research* 4:3029–3038 (No. 9, Sep. 1977).
Russo, N., Ravi Acharya, K.R., Vallee, B.L., & Shaprio, R. Jan. 1996, *Proc. Natl. Acd. Sci USA* 93:804–808.
Shapiro, R., Fett, J.W., Strydom, D.J. & Vallee, B.L. *Biochemistry* 25:7255–7264 (No. 23, 1986). Month of publication data is unavailable.
Irie, M. Watanabe, H., Ohgi, K., Tobe, M. Matsumura, G., Arata, Y., Hirose, T. & Inayama 1984 *J. Biochem*, 95, 751–759 (Issue No. 3). Month of publication data is unavailable.
Zegers, I., Maes, D., Dao–Thi, M.H., Poortmans, F., Palmer, R. & Wyns, L. 1994, *Protein Science* 3:2322–2339. Month of publication data is unavailable.
Wodak, S.Y., Liu,.M.Y, Wyckoff, H.W. 1977, *J. Mol. Biol.* 116:855–875. Month of publication data is unavailable.
Pavloskhy, A.G., Borisova, S.N., Borisov, V.V., Antonov, I.V., Karpeisky, M.Y. Aug. 1978, *FEBS Lett.* 92:258–262.
Moffatt, J.G. & Khorana, H.G., 1961, *J. Am Chem. Soc.* 83:663–675 (Feb. 5, 1961).
Chemical Abstract Search, (1996). Month of publication data is unavailable.
Lee et al., "Kinetic Characterization of Two Active Mutants of Placental Ribonuclease Inhibitor That Lack Internal Repeats," *Biochemistry*, 29(28), 6633–6638 (Jul. 17, 1990).
Russo et al., "A Combined Kinetic and Modeling Study of the Catalytic Center Subsites of Human Angiogenin," *Proc. Nat. Acad. Sci. USA*, 93(2), 804–808 (Jan. 23, 1996).
Strydom et al., "An Angiogenic Protein from Bovine Serum and Milk—Purification and Primary Structure of Angiogenin–2," *European J. Biochem.*, 247(2), 535–544 (Jul. 1997).
Hu et al., "A Putative Angiogenin Receptor in Angiogenin–Responsive Human Endothelial Cells," *Proc. Nat. Acad. Sci. USA*, 94(6), 2204–2209 (Mar. 18, 1997).
Witzel et al., "Mechanism and Binding Sites in the Ribonucleuse Reaction II. Kinetic Studies on the First Step of the Reaction," *Biochem. Biophys. Research Comm.*, 7(4), 295–299 (1962).

*Primary Examiner*—John Kight
*Assistant Examiner*—L. Eric Crane
*Attorney, Agent, or Firm*—Banner & Witcoff Ltd.

[57] ABSTRACT

A method of inhibiting ribonucleases is disclosed wherein a nucleotide compound having a diphosphate group contacts a ribonuclease so as to inhibit the ribonuclease from effectively catalyzing the depolymerization of ribonucleic acid. Novel compounds useful in the method are also disclosed.

16 Claims, 1 Drawing Sheet

5,852,001

METHOD AND COMPOUNDS FOR INHIBITION OF RIBONUCLEASES

This application was funded in part by National Institutes of Health grant no. RO HL 52096O1A2.

BACKGROUND OF THE INVENTION

1. Field of the Invention

Embodiments of the present invention relate in general to compounds and methods that are useful in inhibiting enzymes that effectively catalyze the depolymerization of ribonucleic acid, such enzymes being commonly referred to as "ribonucleases". More particularly, embodiments of the present invention relate to low molecular weight inhibitors of ribonucleases.

2. Description of Related Art

Many procedures in molecular biology and biotechnology involve the use of ribonucleic acid (RNA). It is well known in the art that RNA can be extracted from living cells and tissues, or synthesized in vitro by chemical and/or enzymatic procedures. Purified RNA, from mammalian, bacterial or other sources, may then be used in nucleic acid hybridization techniques and in enzymatic reactions such as those disclosed by Sambrook, J. et al., 1989, *Molecular Cloning: a Laboratory Manual*, Cold Spring Harbor Laboratory Press, Cold Spring Harbor, N.Y.; Glover, D. M., 1985, *DNA Cloning*, IRL Press at Oxford University Press, N.Y.

RNA, however, is very sensitive to degradation by ribonucleases, which are very resistant to inactivation and represent a common contaminant of laboratory equipment and glassware thereby posing a significant problem when intact RNA is required during experimental procedures. For this reason, ribonuclease inhibitors are frequently used to minimize the enzymatic degradation of RNA both during its preparation and its subsequent use.

The structure and properties of a wide variety of potent ribonucleases have been studied. See Beintema, J. J., 1987, *Life Chemistry Reports* 4:333–389, and Richards, F. M. & Wyckoff, H. W., 1971, *Enzymes* 4:647–806. It has been shown that pancreatic ribonucleases, at pH values from 4 to 10, rapidly cleave RNA at their phosphodiester bonds endonucleolytically, via 2', 3'-cyclic phosphate intermediates, to yield oligonucleotides terminating in Cp or Up. Each phosphodiester group comprises a single phosphate group bonded to the 3' carbon of one ribose group and the 5' carbon of the next ribose group. It is well known in the art that ribonucleases possess binding sites for pyrimidine bases, purine bases, riboses and phosphate groups of natural substrates that contribute to the enzymatic activity of the ribonuclease. It is believed that in mammalian pancreatic ribonucleases, including human pancreatic ribonucleases, these binding sites are fully conserved or largely vary only in substitution of amino acid residues that do not substantially alter the polarity or other properties of the site (termed "conservative replacements"). Hence, only minor differences exist among these ribonucleases as to their specific activity in the depolymerization of RNA substrates. Moreover, it is believed that the most important binding sites of non-pancreatic type ribonucleases in the mammalian pancreatic ribonuclease superfamily of proteins are similar or identical to those in pancreatic ribonucleases. Non-pancreatic ribonucleases include human ribonuclease-2 (a major ribonuclease in eosinophils, blood plasma, urine and tissue such as liver, placenta, and spleen—also known as RNase $U_s$ and eosinophil-derived neurotoxin) and ribonuclease-4 (found in the liver and blood of several mammalian species).

There are reports of identification of certain binding sites for nucleosides, nucleotides and oligonucleotides with respect to ribonucleases; however, there exist no standard criteria for predicting whether or how strongly a particular oligo- or polynucleotide will bind as an inhibitor of ribonuclease towards RNA. Nogués et al., 1995, *Biochim. Biophys. Acta* 1253:16–24 has provided commonly accepted nomenclature for the binding sites of ribonucleases. In particular, binding sites of a ribonuclease, such as bovine pancreatic ribonuclease A, that bind bases are designated $B_0$, $B_1$, $B_2$ . . . $B_n$. The subscript in each of the B binding sites refers to the relative position of the base along the RNA substrate proceeding in the 5' to the 3' direction of the polynucleotide chain. The $B_1$ site interacts with the base whose ribose contributes its 3' oxygen to the scissile phosphodiester bond and $B_2$ binds the base whose ribose provides the 5' oxygen. The $B_1$ binding site has a nearly absolute specificity for pyrimidine bases, whereas $B_2$ and $B_3$ prefer purine bases. The sites for binding the ribose moieties attached to the various bases of the substrate are designated $R_0$, $R_1$, $R_2$, . . . $R_n$, respectively. Similarly, the sites for binding the phosphate moieties of the substrate are termed $p_0$, $p_1$, $p_2$, . . . $p_n$. The subscript in each of the p sites refers to the relative position of the phosphate group along the substrate, in the same manner as for base and ribose binding sites. P-O(5') bond cleavage occurs at the $p_1$ site. It is reported that Thr-45, Phe-120 and Ser-123 are present at the B1 binding site of ribonuclease A and may be responsible for interacting with a pyrimidine base such as cytosine or uracil of an RNA substrate. It is further reported that Gln-69, Asn-71 and Glu-111 are present at the $B_2$ binding site of ribonuclease A and may be responsible for interacting with a purine base such as adenine or guanine, but may also interact with cytosine or uracil, or an RNA substrate. Likewise, it is reported that Lys-1 is present at the $B_3$ binding site of ribonuclease A and may be responsible for interacting with a purine base of RNA. Regarding the phosphate binding sites, it is reported that Lys-66 is present at the $p_0$ binding site, Lys-41, His-119, His-12 are present at the $p_1$ binding site, and Lys-7 and Arg-10 are present at the $p_2$ binding site of ribonuclease A and may be responsible for interacting with respective phosphodiester groups of RNA.

The inhibitory activities of ribonuclease inhibitors are commonly compared with respect to RNase A, the most extensively studied of the ribonuclease superfamily, and one of the most effective ribonuclease enzymes (see Eftink, M. R. & Biltonen, R. L., 1987, *Hydrolytic Enzymes*, 333–376). One such RNase A inhibitor, Placental Ribonuclease Inhibitor (PRI), is a 50 kDa protein (See Lee, F. S. & Vallee, B. L., 1993, *Progress in Nucleic Acid Research and Molecular Biology* 44:1–30) commercialized by Promega Co. PRI, which is purified from human placenta or produced in a recombinant form from *E. coli*, is commonly used as a ribonuclease inhibitor only in small volume reactions, such as in vitro transcription, in vitro translation, and cDNA synthesis. PRI is not used for many other applications, e.g. to protect RNA during its extraction from cells and tissues, because it is very sensitive to denaturing agents, air oxidation and heat.

Cytidine 2'-monophosphate (2'-CMP) is a low molecular weight pyrimidine nucleotide inhibitor of RNase A (see Richards, F. M. & Wyckoff, H. W., supra), but it is not routinely used to protect RNA during reactions since its inhibition constant $K_i$ of 147 $\mu$M at pH 7 is much too high to provide complete inhibition at a concentration that is practical to employ. Among other low molecular weight ribonuclease inhibitors, uridine-vanadate (U-V) has the best reported $K_i$, 10 μM at pH 7 (see Lindquist, R. N. et al., 1973, *Journal of the American Chemical Society* 95:8762–8768; Wlodawer, A. et al., 1983, *Proc. Natl. Acad. USA* 80:3628–3631). This complex is generally used together with the vanadyl complexes of adenosine, guanosine, and cytidine and is prepared by mixing the ribonucleosides with a stoichiometric amount of oxovanadium IV ion (see Berger, S. L. & Birkenmeier, 1979, *Biochemistry* 18:5143–5149). The inhibitor mixture is commercialized by Sigma Co. and New England Biolabs and is mainly used during RNA extraction from cells and tissues (e.g., sucrose gradient fractionation, etc.). The mixture is only partially effective at protecting RNA from degradation at concentrations that are practical to employ, and generally is not used during the enzymatic manipulation of RNA because vanadate is also a potent inhibitor of other enzymes.

Other low molecular weight inhibitors of RNase A, whether in the form of free bases, nucleosides or nucleotides, do exist such as those disclosed by Richards, F. M. & Wyckoff, H. W., supra; Irie, M. et al, 1984, *J Biochem.* 95:751–759; Iwahashi, K. et al., 1981, *J Biochem.* 90:1685–1690; and White, M. D. et al., 1977, *Nucleic Acid Research* 4:3029–3038, however, none of these is more effective than U-V and most are much less effective. As demonstrated by the data presented in the above references, there is at present no predictable or standard method for modifying existing inhibitors to improve their effectiveness.

Accordingly, there is a need in the art to provide effective ribonuclease inhibitors which overcome the drawbacks of existing ribonuclease inhibitors in terms of useful and greater activity and specificity, while maintaining ease and economy of synthesis.

BRIEF SUMMARY OF THE INVENTION

Embodiments of the present invention are directed to methods which are useful in the inhibition of ribonucleases and to novel compounds which are also useful to inhibit ribonucleases. According to the method of the present invention, a ribonuclease is contacted with an inhibiting amount of a compound of formula I

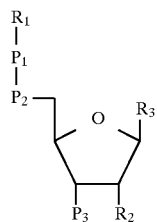

Formula I so as to inhibit the activity of the contacted ribonuclease to enzymatically catalyze the depolymerization of ribonucleic acid.

According to the teachings of the present invention, the ribonuclease is a mammalian ribonuclease in the pancreatic ribonuclease superfamily, $P_1$ and $P_2$ are phosphate groups, $P_3$ is a phosphate or phosphorothioate group, $R_1$ is hydrogen or a substituent capable of occupying the $B_1$ pyrimidine binding site of a ribonuclease, $R_2$ comprises hydrogen or hydroxyl and $R_3$ is a substituent capable of occupying the $B_2$ purine binding site of a ribonuclease. It is to be understood that when $P_1$ and $P_2$ are each phosphate groups, they are collectively referred to as a diphosphate or pyrophosphate group. The term "occupying" as used herein means that the substituent is capable of binding to the binding site as is understood in the art or otherwise interfering with the binding site so as to render the ribonuclease less active with respect to cleavage of RNA substrates.

According to the teachings of the present invention, a compound of formula I is added to a reaction or experimental procedure involving RNA where the presence of one or more ribonucleases is suspected in an amount effective to inhibit the ribonucleases to thereby prevent breakdown of the RNA substrate by the ribonuclease. The amount or concentration of the compound of formula I added will vary depending upon the amount of ribonuclease suspected to be present, the affinity of the ribonuclease for the RNA substrate, and the affinity of the compound for RNase. Preferably, a compound of formula I is added in a 100-fold molar excess above the $K_i$ value so as to ensure that the ribonucleases present will be inhibited.

Embodiments of the present invention are also directed to novel compounds which are useful to inhibit ribonucleases. The compounds are represented by formula I when $P_1$ and $P_2$ are phosphate groups, $P_3$ is a phosphate or phosphorothioate group, $R_1$ is a substituent which is capable of occupying the $B_1$ pyrimidine binding site of a ribonuclease, $R_2$ is hydrogen or hydroxyl and $R_3$ is a substituent capable of occupying the $B_2$ purine binding site of a ribonuclease.

Embodiments of the present invention are advantageous in that they provide methods for inhibiting ribonucleases which are more effective that existing methods. Certain methods of the present invention are further advantageous in that they provide for a greater activity, i.e., in some cases orders of magnitude greater than existing inhibitors, and greater specificity for inhibiting ribonucleases while using small molecule agents which may be more easily and more economically synthesized.

One object of the present invention, therefore, is to provide novel compounds which inhibit ribonucleases. Another object of the present invention is to provide ribonuclease inhibitors which are highly specific. Another object of the present invention is to provide ribonuclease inhibitors which are relatively low in molecular weight and which can be easily and economically synthesized. A further object of the present invention is to provide low molecular weight inhibitors of ribonucleases which have a greater activity as compared to known ribonuclease inhibitors. A still further object of the present invention is to use the novel compounds of the present invention in a method for inhibiting ribonucleases.

Other objects, features and advantages of certain embodiments of the present invention will become more fully apparent from the following description taken in conjunction with the accompanying drawings and claims.

BRIEF DESCRIPTION OF THE DRAWINGS

In the course of the detailed description of certain preferred embodiments to follow, reference will be made to the attached drawings, in which.

DETAILED DESCRIPTION OF CERTAIN PREFERRED EMBODIMENTS

Figure 1:
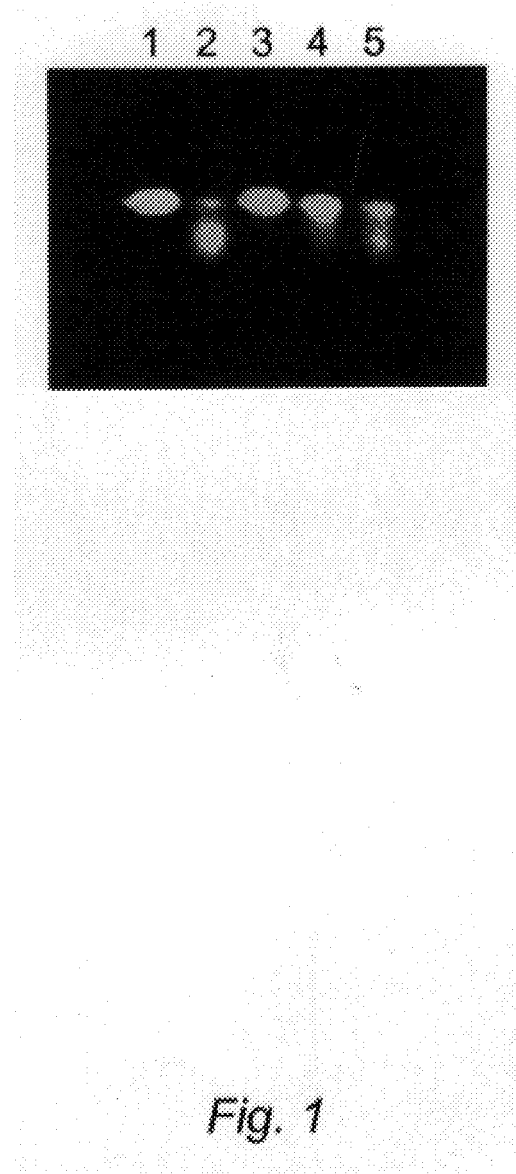
FIG. 1 is a photograph of an electrophoresis gel showing protection of tRNA by an inhibitor of the present invention.

The principles of the present invention may be applied with particular advantage to obtain compounds and methods for inhibiting enzymes which are effective catalysts of the depolymerization of ribonucleic acid. These enzymes are commonly referred to as "ribonucleases" and include, among others, bovine pancreatic ribonuclease A ("RNase") and like ribonucleases. It is to be understood that the methods and compounds of the present invention may be applied to inhibit a broad range of mammalian ribonucleases in the pancreatic ribonuclease superfamily, including human ribonucleases, as will be more readily apparent based on the disclosure to follow, since every potent ribonuclease in the pancreatic ribonuclease superfamily, including human ribonucleases, is believed to have similar unvaried or conserved substrate binding sites or subsites. The methods and compounds of the present invention surprisingly and advantageously provide a greater inhibition of ribonucleases when compared to existing compounds or methods.

The methods of the present invention include contacting a ribonuclease with conserved an inhibiting amount of a small molecule compound of the formula I

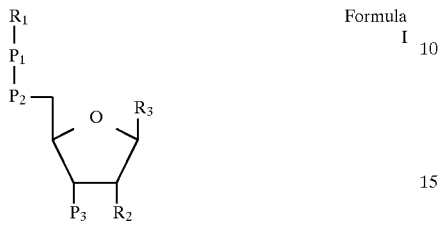

wherein $P_1$ or $P_2$ is a phosphate group, $P_3$ is a phosphate or phosphorothioate group, $R_1$ is hydrogen or is a substituent having a structure which is capable of occupying the $B_1$ pyrimidine binding site of a ribonuclease, $R_2$ is hydrogen or hydroxyl, and $R_3$ is a substituent having a structure which is capable of occupying the $B_2$ purine binding site of a ribonuclease. In a certain preferred embodiment, the chirality of the ribose group as shown in formula I (wherein $R_3$ is attached to the 1' carbon) at the 1' through 4' carbons is R, R, S, R, respectively.

In certain preferred embodiments, $R_1$ is a nucleoside or 5'-phospho-nucleotide, preferably a pyrimidine nucleoside or pyrimidine 5'-phospho-nucleotide, more preferably 2'-deoxyuridine, 2'-deoxythymidine, or 2'-deoxycytidine and most preferably 5'-phospho-2'-deoxyuridine, 5'-phospho-2'-deoxythymidine, or 5'-phospho-2'-deoxycytidine or their phospohorothioate derivatives. $R_3$ is preferably a purine, such as adenine or guanine. It is to be understood that the phosphate groups may be in the acid form or may have a cation attached. It is to be further understood that phosphorothioate derivatives are effective inhibitors and may be used instead of phosphate groups to avoid attack on the compound by phosphatases which may be present during use of the inhibitor.

Certain preferred phosphorothioate compounds wherein one of the nonbridging oxygen atoms in each phosphate portion of the nucleotide is replaced by sulfur as described above are represented by the following structures:

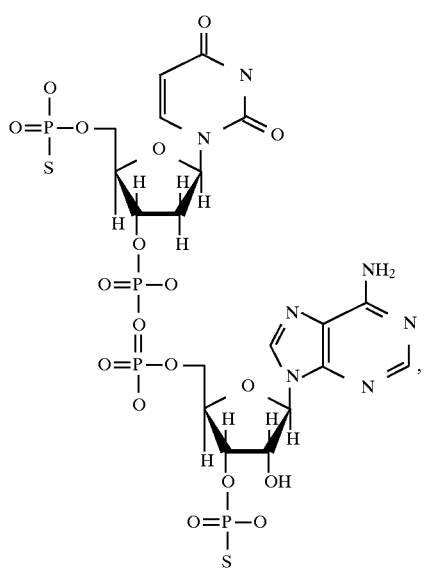

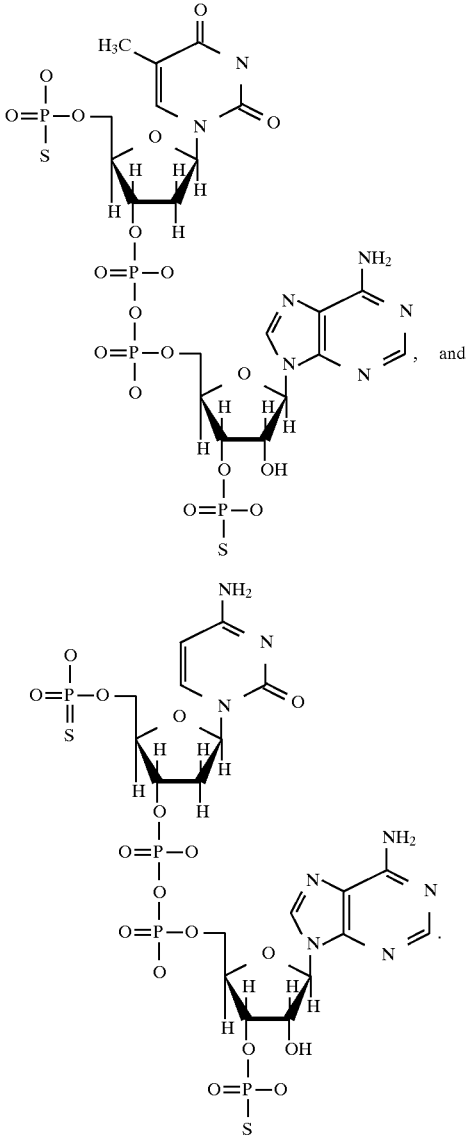

The methods and small molecule compounds of the present invention advantageously provide substituent groups and conformations which occupy, bind to, or otherwise interfere with the subsites of the ribonuclease thereby altering the activity of the ribonuclease with respect to cleavage of ribonucleic acid. For example, the $R_1$ substituent is believed to occupy, bind to, or otherwise interfere with the $B_1$ pyrimidine binding site of a ribonuclease. Likewise, the $R_3$ substituent group is believed to occupy, bind to, or otherwise interfere with the $B_2$ binding site of the ribonuclease.

In addition, it has been unexpectedly discovered that compounds of the present invention having a diphosphate, i.e. pyrophosphate, bridging group between the ribose ring and the $R_1$ group as represented by $P_1$ and $P_2$ of formula I exhibit an unexpectedly increased inhibitory activity with respect to ribonucleases substantially greater than that of known inhibitors of ribonucleases which have only a single phosphate group. This increased inhibitory activity based upon a diphosphate group is neither recognized nor predictable from the structures of nucleotides or oligonucleotides known to be inhibitors of ribonucleases or from known binding sites of ribonucleases. The diphosphate group is believed to provide an advantageous conformation of the compounds of formula I previously unattainable by known inhibitors which allow the various substituents to more effectively occupy, bind to, or otherwise interfere with the ribonuclease. In addition, it is believed that the diphosphate group may also occupy, bind to or otherwise interfere with an active site of a ribonuclease. It has been further unexpectedly discovered that compounds having a phosphate or phosphorothioate moiety as indicated by $P_3$ of formula I also exhibit an increased inhibitory activity as compared to compounds lacking a phosphate or phosphorothioate at that position.

The compounds of the present invention may be employed in amounts sufficient to inhibit the activity of ribonucleases with respect to RNA substrates. The term "RNA" as used herein refers to all ribonucleic acids, mammalian or otherwise, including transfer-RNA, messenger-RNA, ribosomal-RNA and the like where cleavage of a phosphodiester bond occurs. The term "ribonuclease" as used herein includes all ribonucleases of the mammalian pancreatic ribonuclease superfamily (such as those disclosed in Beintema, J. J., 1987, *Life Chemistry Reports* 4:333–389), which effectively catalyze the depolymerization of RNA substrates, since pyrimidine and purine binding sites are known to be unvaried or show only conservative replacements in ribonucleases of the mammalian pancreatic ribonuclease superfamily.

The amount of the compound of the present invention used will vary depending upon the amount of the ribonuclease present and its affinity for an RNA substrate. Typically, standard enzymatic reactions involving RNA are carried out in the 20 to 50 µl volume range. On this scale, a useful concentration of an inhibitor compound of the formula I will range between about 0.1 to 10 mM to inhibit ribonucleases. Higher concentrations can be used due to the high solubility of the compounds of formula I. Typical RNA extraction methods are carried out in the milliliter scale and would also employ a concentration of a compound of formula I of about 0.1 to 10 mM. Alternatively, one may vary the concentration of an inhibitor compound of formula I as a function of the $K_i$ value at a particular pH. Preferably, as a general rule, the concentration of inhibitor employed is 100 fold higher than the $K_i$ value of the inhibitor at the particular pH at which the reaction or experimental procedure is being carried out.

The following examples are set forth as representative of the present invention. These examples are not to be construed as limiting the scope of the invention as these and other equivalent embodiments will be apparent in view of the present disclosure, figures, tables, and accompanying claims.

EXAMPLE 1

Preparation of 5'-diphosphoadenosine-3'-phosphate (ppAp)

5'-diphosphoadenosine-3'-phosphate (ppAp) has been found to be a potent inhibitor of RNase A. The inhibitor compound was tested in an RNA protection assay at a physiological pH and found much more effective than other low molecular weight inhibitors, including the transition-state analogue uridine-vanadate. The adenosine based structure of ppAp is expected to be able to interact with the purine ($B_2$) binding site of all mammalian RNases in the pancreatic RNase superfamily. These findings confer to ppAp a novel applicability to the binding and inhibition of RNases, for example to protect RNA in molecular biology procedures.

5'-diphosphoadenosine-3'-phosphate was prepared by enzymatic treatment of adenosine 2',3'-cyclic phosphate 5'-diphosphate (ppA>p) with $T_2$ RNase from *Aspergillus oryzae*. 15 mg of the triethylammonium salt of ppA>p (see Russo et al., 1996, *Proc. Natl. Acad. Sci. USA* 93:804–808) were dissolved in 2.5 ml of 0.1M Mes buffer (pH 5.9) containing 20 units of $T_2$ RNase (grade VII, from Sigma). After 5 h of incubation at 37° C., the reaction mixture was loaded onto a QAE-Sephadex column (1.5×5 cm) which had been equilibrated with 0.1M triethylammonium bicarbonate buffer (TEAB) at pH 7.3 and eluted with a 200-min linear gradient from 0.1 to 0.4M TEAB, at a flow rate of 2 ml/min. The main peak of absorbance at 280 nm was collected, diluted with an equivalent volume of water, and lyophilyzed. The sample was then dissolved in I ml of methanol and precipitated by the addition of 10 ml of dry ether. The precipitate was collected by centrifugation, dried in vacuo and reconstituted in 1 ml of water. The sample was finally converted from the triethylammonium salt to the sodium salt by passing it through a column (0.5×2 cm) of SP-Sephadex ($Na^+$) in water. The yield of ppAp was 70% based on $C_{18}$/HPLC quantitation of the adenosine produced by digesting an aliquot with calf intestinal phosphatase. The purity of the final product was 94% as judged by anion-exchange Mono-Q/HPLC chromatography with a 25-min linear gradient from 25 to 400 mM NaCl in 10 mM Tris-Cl (pH 8) at a flow rate of 1.2 ml/min recording absorbance at 254 nm. Most of the contaminant material coeluted with adenosine 3',5'-diphosphate (pAp). The identity of the final product as ppAp was confirmed by the following evidence: (i) the sample eluted from the Mono-Q column 3 minutes later than pAp, indicating it is more negatively charged, and (ii) its digestion with an excess of inorganic pyrophosphatase produces pAp.

The corresponding guanosine-based structure may be prepared according to the method outlined above, except that guanosine 2',3'-cyclic phosphate 5'-diphosphate will be used instead of the adenosine-based starting material.

EXAMPLE II

Measurement of the inhibition constant of RNase A for ppAp

The ppAp produced in accordance with Example I above was initially tested for the ability to inhibit the activity of RNase A toward cytidylyl-(3',5')-adenosine (CpA), a synthetic substrate commonly employed for the determination of kinetic parameters of ribonucleases. Assays were performed in 60 µl of 0.2M Mes (pH 5.9) containing 50 µg/ml nuclease-free bovine serum albumin (obtained from Worthington), 20 µM CpA, and 23–320 pM RNase A. After 14–96 minutes of incubation at 25° C., substrate and products were quantitated by $C_{18}$/HPLC with a 20 minute linear gradient from 0 to 5.6% acetonitrile in 0.1% trifluoroacetic acid at a flow rate of 1.5 ml/min recording absorbance at 254 nm. Values of $K_m/k_{cat}$ were then calculated (according to the method of Shapiro et al., 1986, *Biochemistry* 25:7255–7264) and plotted vs. the inhibitor concentration [I]. The $K_i$ value is the -[I] intercept of a three- or four-point plot of $K_m/k_{cat}$, vs. [I] and was obtained by linear regression. According to the results presented in Table I below, the $K_i$ of RNase A for ppAp was found to be 0.24 µM which is 23- and 13- fold lower than those measured in the same reaction conditions for adenosine 3',5'-diphosphate (pAp)(as discussed in Irie, M. et al., supra) and 2'-CMP, respectively, indicating that ppAp is a stronger and more potent inhibitor of RNase A.

TABLE I

| Inhibitor | $K_i$ ($\mu M$) |
| --- | --- |
| Cytidine 2'-monophosphate (2'-CMP) | 3.1 |
| Adenosine 3',5'-diphosphate (pAp) | 5.6 |
| 5'-diphosphoadenosine 3'-phosphate (ppAp) | 0.24 |

The value of the ratio between the $K_m$ of RNase A for CpA and the $K_i$ value for ppAp is about 1000, implying that the affinity of RNase A for ppAp is about 1000-fold higher than that for CpA substrate. It has been discovered that the addition of a β-5'-phosphate to pAp, yielding ppAp, provides unexpected and significantly greater inhibitory properties. It is believed that the additional phosphate group provides additional interactions with a ribonuclease previously unrecognized and unattainable with a standard single phosphate group of a nucleotide or phosphodiester group of an oligonucleotide.

EXAMPLE III

RNA protection assay

The ppAp inhibitor was subsequently tested for the ability to protect transfer RNA (tRNA, a natural polymeric RNA) from the hydrolytic activity of RNase A at a physiological pH. 3 μg of tRNA were incubated in 30 μl of 20 mM Hepes, 130 mM NaCl (pH 7.0) containing 30 μg/ml bovine serum albumin, 0.2 nM RNase A and the inhibitor. After 20 minutes of incubation at 25° C., the reaction mixture was analyzed by agarose gel electrophoresis and staining with ethidium bromide. This assay was chosen since a single endonucleolytic cleavage in a polymeric RNA molecule can produce a large variation of the molecular size which can be easily detected by agarose gel electrophoresis. In FIG. 1, lane 1 is undigested tRNA, lane 2 is tRNA digested in the absence of inhibitor, lanes 3 through 5 are tRNA digested in the presence of ppAp, 2'-CMP, and uridine-vanadate, respectively. As shown in FIG. 1, ppAp was found to be a very effective inhibitor since 0.5 mM concentration of ppAp was capable of fully protecting tRNA from the catalytic action of RNase A while the same concentration of 2'-CMP and U-V can only produce a partial protection.

EXAMPLE IV

Binding of ppAp to RNase A

As discussed previously, the ribonucleolytic center of RNase A is believed to contain various subsites for binding of the phosphate and base moieties of the substrate. See Nogues, M. V. et al., 1995, *Biochimica et Biophysica Acta* 1253:16–24): (i) a $p_1$ site where the phosphodiester bond cleavage occurs, (ii) a $B_1$ site where binding of the pyrimidine moiety of the nucleoside with the scissile 3' oxygen occurs, (iii) a $B_2$ site where binding of the base of the nucleoside with the scissile 5' oxygen occurs, (iv) a $P_2$ site for binding the 3'-phosphate of the nucleotide bound in $B_2$, and (v) $p_0$ and $B_3$ sites for binding of a peripheral phosphate and base components of the substrate, respectively. X-ray crystallographic studies with RNase A have shown that the adenosine moiety of previous nucleotide inhibitors invariably binds to the $B_2$ site (Zegers, I. et al., 1994, *Protein Science* 3:2322–2339; Richards, F. M. & Wyckoff, H W., 1973, in *Atlas of Molecular Structures in Biology* Vol. 1; Wodak, S. Y. et al., 1977, *J. Mol. Biol.* 116:855–875; Pavlovsky, A. G. et al., 1978, *FEBS Lett.* 92:258–262.).

As previously stated, the inhibitors of the present invention are believed to provide advantageous substituent groups and/or conformations which occupy, bind to, or otherwise interfere with the subsites of a ribonuclease in a manner different from known inhibitor compounds and which result in increased inhibitory activity when compared with known inhibitor compounds. Accordingly, X-ray crystallographic studies on the complex of ppAp and ribonuclease A have been performed according to methods well known in the art to confirm that the inhibitors of the present invention bind and/or interact differently with ribonucleases when compared with previous inhibitors. The data generated as a result of those studies indicate that while the adenine of ppAp binds to the $B_2$ site of the ribonuclease, it does so in a conformation unlike that described for previous nucleotide inhibitors. The adenine is rotated about the glycosidic bond by almost 180° compared to previous inhibitors that bind to the $B_2$ site. Consequently, the interactions of the adenine ring with RNase A are largely different from those reported for previous inhibitors. In addition, the 5'-β-phosphate binds to the $p_1$ site while the 5'-α-phosphate interacts with residues adjacent to the $p_1$ site, with the 3'-phosphate occupying the $p_2$ site. In previously described complexes, it is the 5'-α-phosphate that binds to the $p_1$ site. The ribose ring of ppAp is also shifted significantly compared to adenosine riboses of previous inhibitors. The mode and conformation of interaction between inhibitors of the present invention and ribonucleases is believed to account for the observed increase in activity and greater specificity of the inhibitors of the present invention when compared with previous nucleotide inhibitors.

EXAMPLE V

2'-deoxyuridine-(3'-$P_\beta$)-5'-diphosphoadenosine-3'-phosphate

A derivative of ppAp—having a pyrimidine substituent linked to the 5'-β-phosphate—has been prepared and tested for inhibition of RNase A. The new compound, 2'-deoxyuridine-(3'-$P_\beta$)-5'-diphosphoadenosine-3'-phosphate (dUppAp), was prepared by a combined chemical and enzymatic procedure. Adenosine 2',3'-cyclic phosphate 5'-phosphomorpholidate was prepared as described in Moffat, J. G. and Khorana, H. G., 1961, *J. Am. Chem. Soc.* 83:663–675 and then incubated with 3 equivalents of 2'-deoxyuridine 3'-monophosphate in anhydrous pyridine, for 15 h at room temperature. The reaction product was treated with $T_2$ RNase (grade VII, from Sigma), and finally purified by anion-exchange chromatography as previously described for the purification of ppAp. The identity of the final product as dUppAp was confirmed by the following evidence: enzymatic digestion of dUppAp with nucleotide pyrophosphatase (E.C. 3.6.1.9.) produces pAp and 2'-deoxyuridine 3'-phosphate (dUp).

A structural isomer of dUppAp, 2'-deoxyuridine-(3'-$P_\beta$)-5'-diphosphoadenosine-2'-phosphate (dUppA2'p) was also prepared and tested for inhibition of RNase A. The synthesis of this compound was performed by the same procedure described above for dUppAp, except that a digestion with 2',3'-cyclic nucleotide 3'-phosphodiesterase was substituted for the enzymatic treatment with $T_2$ RNase.

EXAMPLE VI

5'-phospho-2'-deoxyuridine-(3'-$P_\beta$)-5'-diphosphoadenosine-3'-phosphate A derivative of dUppAp—having a phosphate bound to the 5'-OH of the uridine—has been prepared and tested for inhibition of RNase A. The new compound, 5'-phospho-2'-deoxyuridine-(3'-$P_\beta$)-5'-diphosphoadenosine-3'-phosphate (pdUppAp), was prepared by phosphorylation of dUppAp with $T_4$ polynucleotide kinase (obtained from Promega). The identity of the product as pdUppAp was confirmed by the following evidence: (i) the sample eluted from an anion-exchange Mono-Q column several minutes later than dUppAp, indicating it is more negatively charged; (ii) enzymatic digestion of pdUppAp with nucleotide pyrophosphatase (E.C. 3.6.1.9) produces pAp and a second compound having an elution time from a Mono-Q column slightly shorter than that of 5'-phosphouridine 3'-phosphate (pUp), as expected for 5'-phospho 2'-deoxyuridine 3'-phosphate (pdUp).

EXAMPLE VII

5'-phosphothymidine-(3'-$P_\beta$)-5'-diphosphoadenosine-3'-phosphate

A derivative of ppAp—having a pyrimidine substituent linked to the 5'-β-phosphate—has been prepared and tested for inhibition of RNase A. The new compound, 5'-phosphothymidine-(3'-$P_\beta$)-5'-diphosphoadenosine-3'-phosphate (pTppAp), was prepared by the same procedure described above for pdUppAp, except that thymidine 3'-monophosphate was substituted for 2'-deoxyuridine 3'-monophosphate in the first chemical reaction. The identity of the final product as pTppAp was confirmed by the following evidence: (i) the sample eluted from an anion-exchange Mono-Q column several minutes later than ppAp, indicating it is more negatively charged; (ii) enzymatic digestion of pTppAp with nucleotide pyrophosphatase produces pAp and 5'-phosphothymidine 3'-phosphate (pTp).

EXAMPLE VIII

Thymidine-(3'-$P_\beta$)-5'-diphospho-2'-deoxyadenosine

Another dinucleotide with a pyrophosphate linkage has been prepared and tested for inhibition of RNase A. The new compound, thymidine-(3'-$P_\beta$)-5'-diphospho-2'-deoxyadenosine (TppdA), was prepared as follows. 75 mg of 2'-deoxyadenosine 5'-phosphomorpholidate (Sigma) were incubated with 100 mg of the tributylammonium salt of thymidine 3'-monophosphate (Tp) in 3 ml of dry pyridine at room temperature. After 24 hours the reaction mixture was loaded onto a QAE-Sephadex column (1.5×5 cm) which had been equilibrated with 0.1M triethylammonium bicarbonate buffer (TEAB) at pH 7.3 and eluted with a 100 minute linear gradient from 0.1 to 0.25M TEAB, at a flow rate of 2 ml/min. The main peak of absorbance at 280 nm was diluted with an equal volume of water, lyophilyzed, redissolved in 1 ml of methanol, precipitated by the addition of 10 ml of dry ether, and finally reconstituted in water. The identity of the final product as TppdA was confirmed by enzymatic digestion with nucleotide pyrophosphatase and subsequent identification of reaction products as Tp and 2'-deoxyadenosine 5'-phosphate (pdA). The inhibitory activity of TppdA, having a pyrophosphate group, was compared with a similar compound having only a phosphate bridging group. The compound, thymidylyl-(3'-5')-2'-deoxyadenosine (TpdA), was purchased from Sigma and the value for its $K_i$ was determined by an HPLC method, as described in Example II and is presented in Table II below.

EXAMPLE IX

Inhibition of Ribonuclease

The inhibition of RNase A by ppAp, dUppAp, dUppA2'p, pdUppAp, pTppAp, and TppdA at various pH values was measured by a modification of the spectrophotometric method of Witzel and Barnard (see Witzel, H. & Barnard, E. A., 1962, *Biochem. Biophys. Res. Commun.* 7:295–299). Assays were performed at 25° C. with the dinucleotide cytidylyl-(3',5')-guanosine (75 µM) as substrate in 0.2M Mes (pH 5.9), 0.2M Hepes (pH 7.0), or 0.2M Hepes (pH 8.0), containing 10 µg/ml bovine serum albumin. The decrease in absorbance at 286 nm following the addition of RNase A was continuously monitored. Inhibition was assessed from the dependence of $1/v_0$ on [I], where $v_0$ represents the velocity measured during the initial 5–10% of the enzymatic reaction and [I] is the inhibitor concentration. Since the substrate concentration used in these assays is well below $K_m$, the -[I] intercept of such a plot should closely approximate $K_i$ for simple inhibition mechanisms.

As shown in Table II below, dUppAp, pdUppAp and pTppAp were found to be more effective inhibitors of RNase A than is ppAp. The RNase A inhibition constant for pdUppAp at pH 5.9, pH 7, and pH 8 is lower than that for ppAp by factors of 6.9, 6.2, and 9.9, respectively. The RNase A inhibition constant for pTppAp at pH 5.9, pH 7 and pH 8 is lower than that for ppAp by factors of 4.6, 7.2 and 7.8, respectively. Moreover, the $K_i$ values for ppAp, pdUppAp and pTppAp at pH 7 are lower than the 10 µM $K_i$ for uridine-vanadate (Lindquist et al., supra) by factors of 7.7, 48 and 56, respectively.

TABLE II

| | $K_i$ (µM) at indicated pH | | |
|---|---|---|---|
| Inhibitor | pH 5.9 | pH 7 | pH 8 |
| ppAp | 0.24 | 1.3 | 217 |
| dUppAp | 0.13 | 1.1 | 44 |
| dUppA2'p | 0.66 | | |
| pdUppAp | 0.035 | 0.21 | 22 |
| pTppAp | 0.052 | 0.18 | 28 |
| TpdA | 1300 | | |
| TppdA | 3.5 | | |

It is to be understood that additional $K_i$ values for each compound may be determined at various other pH values based upon the teachings of the present invention demonstrating that the compounds of the present invention are useful inhibitors at pH values other than the ones specifically identified above.

As further indicated in Table II, the corresponding $K_i$ values for TpdA and TppdA, i.e., 1300 µM and 3.5 µM respectively, demonstrate that the diphosphate group of TppdA advantageously and dramatically provides a compound with increased ribonuclease inhibiting activity orders of magnitude greater than TpdA.

Finally, it should be noted that the $K_i$ for dUppA2'p is 5-fold higher than that for dUppAp. This difference in $K_i$ indicates that the presence of a phosphate in the 2'-position of the adenosine rather than in the 3'-position markedly decreases inhibitor binding to RNase A.

EXAMPLE X

Inhibition of Human Ribonucleases

The ppAp, pdUppAp and pTppAp compounds of the present invention were tested for the inhibition of two potent human ribonucleases, hRNase-2 and hRNase-4 according to the methods previously described in Example IX. The results presented in Table III below at pH 5.9 demonstrate that the compounds of the present invention are also effective inhibitors of the human ribonucleases.

TABLE III

| Inhibitor | $K_i$ ($\mu$M) at pH 5.9 | |
| --- | --- | --- |
|  | hRNase-2 | hRNase-4 |
| ppAp | 0.25 | 0.54 |
| pdUppAp | 0.22 | 0.28 |
| pTppAp | 0.50 | 0.27 |

It is to be understood that the embodiments of the present invention which have been described are merely illustrative of some of the applications of the principles of the invention. Numerous modifications may be made by those skilled in the art based upon the teachings presented herein without departing from the true spirit and scope of the invention.

What is claimed is:

1. A compound of the formula:

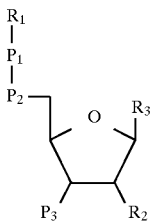

wherein:
- $P_1$ is a phosphate group;
- $P_2$ is a phosphate group;
- $P_3$ is a phosphate or phosphorothioate group;
- $R_1$ is a 3'-linked nucleoside or 5'-phospho-nucleotide;
- $R_2$ is hydrogen or hydroxyl; and
- $R_3$ is a purine.

2. A compound according to claim 1, wherein $R_1$ is a pyrimidine nucleoside or pyrimidine 5'-phospho-nucleotide and $R_3$ is adenine or guanine.

3. A compound according to claim 2 wherein $R_1$ is 5'-phospho-2'-deoxycytidine or 5'-phosphorothio-2'-deoxycytidine.

4. A compound according to claim 2, wherein $R_1$ is 2'-deoxyuridine.

5. A compound according to claim 2 wherein $R_1$ is 5'-phospho-2'-deoxyuridine or 5'-phosphorothio-2'-deoxyuridine.

6. A compound according to claim 2, wherein $R_1$ is 2'-deoxythymidine.

7. A compound according to claim 2 wherein $R_1$ is 5'-phospho-2'-deoxythyridine or 5'-phosphorothio-2'-deoxythymidine.

8. A compound according to claim 2, wherein $R_1$ is 2'-deoxycytidine.

9. A method of inhibiting a ribonuclease of the mammalian pancreatic ribonuclease superfamily comprising contacting the ribonuclease with an inhibiting amount of a compound of formula I

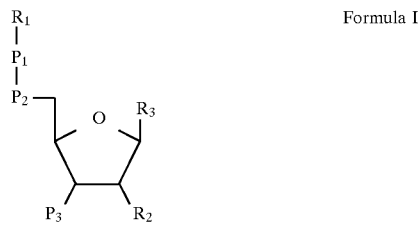

wherein:
- $P_1$ is a phosphate group;
- $P_2$ is a phosphate group;
- $P_3$ is a phosphate or phosphorothioate group;
- $R_1$ is hydrogen or a 3'-linked nucleoside or 5'-phospho-nucleotide;
- $R_2$ is hydrogen or hydroxyl; and
- $R_3$ is a purine.

10. A method according to claim 9, wherein $R_1$ is a pyrimidine nucleoside or pyrimidine 5'-phospho-nucleotide and $R_3$ is adenine or guanine.

11. A compound according to claim 10, wherein $R_1$ is 2'-deoxycytidine.

12. A compound according to claim 10 wherein $R_1$ is 5'-phospho-2'-deoxycytidine or 5'-phosphorothio-2'-deoxycytidine.

13. A method according to claim 10, wherein $R_1$ is 2'-deoxyuridine.

14. A method according to claim 10 wherein $R_1$ is 5'-phospho-2'-deoxyuridine or 5'-phosphorothio-2'-deoxyuridine.

15. A method according to claim 10, wherein $R_1$ is 2'-deoxythymidine.

16. A method according to claim 10 wherein $R_1$ is 5'-phospho-2'-deoxythymidine or 5'-phosphorothio-2'-deoxythymidine.

* * * * *

UNITED STATES PATENT AND TRADEMARK OFFICE
CERTIFICATE OF CORRECTION

PATENT NO. : 5,852,001

DATED : December 22, 1998

INVENTOR(S) : Vallee et al.

It is certified that error appears in the above-identified patent and that said Letters Patent is hereby corrected as shown below:

col. 1 lines 1 and 2, delete "This application was funded in part by National Institutes of Health grant no. RO HL 5209601A2."

Signed and Sealed this

Eleventh Day of April, 2000

Attest:

Q. TODD DICKINSON

Attesting Officer

Director of Patents and Trademarks